United States Patent di Schiena et al.

[11] 4,387,096
[45] Jun. 7, 1983

[54] CEPHALOSPORINE COMPOUNDS WITH ANTIBIOTIC ACTIVITY

[75] Inventors: Michele di Schiena; Vittoria Orru, both of Trezzano sul Naviglio (Milan), Italy

[73] Assignee: Ausonia Farmaceutici s.r.l., Rome, Italy

[21] Appl. No.: 279,456

[22] Filed: Jul. 1, 1981

[30] Foreign Application Priority Data

Jul. 15, 1980 [IT] Italy ............................. 23455 A/80

[51] Int. Cl.³ .................. C07D 501/38; A61K 31/545
[52] U.S. Cl. ................................... 424/246; 544/25; 544/27
[58] Field of Search ................ 544/27, 28, 25, 21, 544/30; 424/246

[56] References Cited

U.S. PATENT DOCUMENTS

| | | | |
|---|---|---|---|
| 4,008,246 | 2/1977 | Ochiai et al. | 544/27 |
| 4,080,498 | 3/1978 | Numata et al. | 544/27 |
| 4,172,891 | 10/1979 | Numata et al. | 544/25 |

Primary Examiner—Nicholas S. Rizzo
Attorney, Agent, or Firm—Bucknam and Archer

[57] ABSTRACT

New derivatives of 1,3-thiazolidin-4-yl carboxylic acid of the general formula I

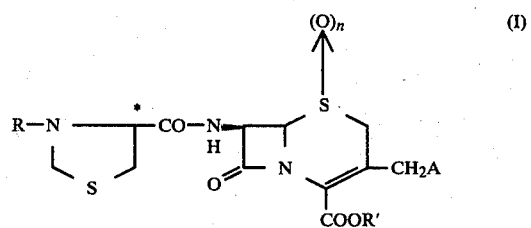

wherein:
R represents hydrogen, (C$_{1-4}$)alkyl, aralkyl, phenyl, phenyl substituted by a halogen atom or a methoxy group, formyl, acyl, trimethylsilyl;

R' represents hydrogen, a pharmaceutically acceptable inorganic or organic cation, (C$_{1-4}$)alkyl, 2,2,2-trichloroethyl, acetonly, benzyl, benzyl substituted by nitro or methoxy, phenyl, nitrophenyl, benzhydryl or trimethylsilyl;

R' may also represent a radical capable of providing metabolic activation in vivo selected from acetoxymethyl, pivaloyloxymethyl, phthalidyl, benzoyloxymethyl, 5-indanyl, a group of formula

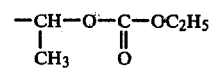

or a group of formula

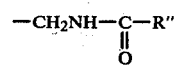

in which R" stands for (C$_{1-4}$)alkyl, (C$_{5-6}$)cycloalkyl or aryl;

A represents hydrogen, halogen, N$_3$, OH, NH$_2$; or a quaternary N-atom, particularly

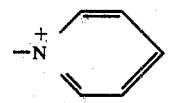

in this case R' is a negative charge); or a O—CO—NH$_2$ group; or a group of the formula OR''', O—COR''', NH—CO—R''' or SR''', where R''' is (C$_1$-C$_4$)alkyl, aryl, substituted aryl or a heterocyclic group which can carry lower alkyls;
n may be zero or 1.

The compounds possess antibacterial utility against microbial infections in man, animals and plants.

12 Claims, No Drawings

CEPHALOSPORINE COMPOUNDS WITH ANTIBIOTIC ACTIVITY

DESCRIPTION OF THE INVENTION

The present invention refers to new 1,3-thiazolidin-4-yl-carboxylic acid derivatives of the general formula I

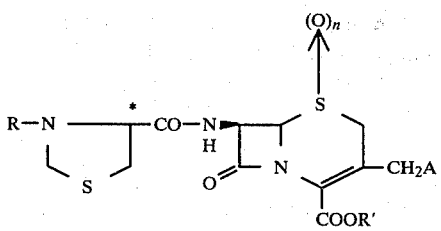

wherein:

R represents hydrogen, $(C_{1-4})$alkyl, aralkyl, phenyl, phenyl substituted by a halogen atom or a methoxy group, formyl, acyl, trimethylsilyl;

R' represents hydrogen, a pharmaceutically acceptable inorganic or organic cation, $(C_{1-4})$alkyl, 2,2,2-trichloroethyl, acetonyl, benzyl, benzyl substituted by nitro or methoxy, phenyl, nitrophenyl, benzhydryl or trimethylsilyl;

R' may also represent a radical capable of providing metabolic activation in vivo selected from acetoxymethyl, pivaloyloxymethyl, phthalidyl, benzoyloxymethyl, 5-indanyl, a group of formula

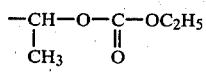

or a group of formula

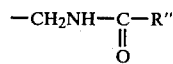

in which R" stands for $(C_{1-4})$alkyl, $(C_{5-6})$cycloalkyl or aryl;

A represents hydrogen, halogen, $N_3$, OH, $NH_2$; or a quaternary N-atom, particularly

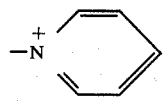

(and in this case R' is a negative charge); or a O—CO—$NH_2$ group; or a group of the formula OR''', O—COR''', NH—CO—R''' or SR''', where R''' is $(C_1-C_4)$alkyl, aryl, substituted aryl or a heterocyclic group which can carry lower alkyls;

n may be zero or 1.

Characteristic meanings assumed by the radical R besides those already illustrated above are selected from methyl, ethyl, isopropyl, benzyl, trityl, acetyl, propionyl, trifluoroacetyl, benzoyl, benzoyl substituted by one to three hydroxy, methyl, methoxy, halo, amino and nitro groups, benzyloxycarbonyl, tert.-butoxycarbonyl or a radical deriving from a natural aminoacid.

Typical, but not limitative examples of the inorganic or organic cations represented by the radical R' are sodium, potassium, calcium and magnesium cations; cations deriving from organic bases such as, for instance, dibenzylamine, N,N-dibenzylethylenediamine, glucamine, N-methylglucamine, hexamethylenetetramine, 2-amino-2-hydroxymethyl-1,3-propanediol, arginine, lysine, proline, carnitine; or aluminum, zinc or silver cations.

Typical meanings of R''', besides those already illustrated above, are selected from methyl, ethyl, propyl, butyl, isobutyl; phenyl or benzyl; imidazol-2-yl, 1,2,3-triazol-5-yl, 1-methyl-1,2,3,4-tetrazol-5-yl, thiazol-2-yl, 1,3,4-thiadiazol-2-yl, 5-methyl-1,3,4-thiadiazol-2-yl, 1,2,3,4-thiatriazol-5-yl, oxazol-5-yl, 3-methylisoxazol-5-yl, 1,2,4-oxadiazol-5-yl, pyrazinyl.

Because of the presence of the asymmetric carbon atom at the 4-position of the thiazolidine ring, the compound of formula I may exist in one of the D- and L-configuration or as a racemic compound. Accordingly the invention contemplates all of these possibilities, though the L-configuration is the preferred one.

A further object of the invention is also represented by the salts of the compounds of formula I, in which the nitrogen atom of the thiazolidine nucleus has basic character, with pharmaceutically acceptable acids, e.g. citric, ascorbic, maleic, acetic, chloridric, nitric, hydrobromic and sulfuric acid.

Another object of the invention is represented by the pharmaceutical compositions for human or veterinary use, or pesticidal formulations for agricultural use containing as the active ingredient one or more of the compounds of formula I above or a pharmaceutically acceptable acid addition salt thereof.

It has been now surprisingly found that the compounds of formula I according to the invention are highly resistant to penicillinases when tested according to the method described by GROVE et al., Assay methods of antibiotics, A Laboratory Manual, Med. Encyclop. Inc., 1955, 7, or according to LORIAN V., Antibiotics and chemotherapeutic agents in clinical and laboratory practice, C. C. Thomas Publ., 1966, 242. They also have proven to be active against various pathogenic agents, e.g. gram-positive and gram-negative, aerobes and anaerobes bacteria, including β-lactamase producing strains.

More particularly, the compounds of formula I are active against gram-positive bacteria such as, for instance, Staphylococcus aureus, Diplococcus pneumoniae, Streptococcus pyogenes, Streptococcus faecalis, Bacillus subtilis and Sarcina lutea, as well as gram-negative bacteria such as, for instance, Escherichia coli, Proteus mirabilis, Shigella sonnei, Klebsiella pneumoniae, Pseudomonas aeruginosa, Haemophilus influenzae and Salmonella typhimurium.

The compounds of formula I according to the invention display also a remarkable activity against various pathogenic agents responsible of infections in vegetables, e.g.: Pseudomonas syringae, responsible of the bacteriosis of citrus-fruits and lilacs; Pseudomonas phaseolicola (halo blight of beans); Pseudomonas aliicola (bacterial mould of onions); Pseudomonas savastandi (scab of olive-trees); Pseudomonas marginata (scab of gladiolus); Xantomonas phaseoli (bacterial mildew of beans); Pectob. carotovorum (stump of potatoes and bacterial mould of iris rhizomes); Erwinia amilovora (necrosis of orchard branches); Erwinia carotovora (bacterial mould of carrots); Corynebacterium flaccum-faciens (bacterial of beans); Penicillum sp. (bacterial mould of bulbs and corms).

As a representative, but not limitative example, it is reported that the 7-(N-pivaloyl-1,3-thiazolidin-4-yl)-carboxamido-cephalosporanic acid (compound of formula I wherein R=(CH3)3C—CO, R'=H, A=O—CO—CH3, n=zero) is endowed with an antibacterial activity (against gram-positive bacteria) corresponding and sometimes better than the one of cephaloridine and cephalexin. Another compound of formula I, that is 7-(N-pivaloyl-1,3-thiazolidine-4-yl)carboxamido)-3-[(5-methyl-1,3,4-thiadiazole-2-yl-thio)methyl]-3-cephem-4-carboxylic acid (R=(CH3)3C—CO, R'=H, A=

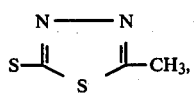

n=zero) is against gram-positive bacteria at least active as cephalexin; but is does not give any resistance, whereas cephalexin induces resistence on S. Aureus strains in a dose of 25 mcg/ml.

Accordingly, the new compounds which are one of the objects of the present invention may be administered to warm blooded animals, including humans, by oral, parenteral or topic route for combatting septicaemiae, meningitis, endocarditis; infections of the respiratory, gastroenteric and genitourinary tract and of the skin; ear-, nose-, throat infections; infections of bones; endoabdominal and endopleurical infections. They may also be employed in the asepsis of the skin before injections or surgical interventions; as well as in the disinfection of surgical tools.

The pharmaceutical dosage forms suitable for the oral administration may be, for instance, tablets, capsules, pills, sugar coated tablets, syrups; suspensions, drops, elixirs and granules. Pharmaceutical dosage forms suitable for the topical use are essentially represented by ointments, cremes, embrocations, collyria and lotions.

All of the above mentioned pharmaceutical formulations are prepared as known in the art and contain, together with the active ingredient, lubricant, diluent, excipient, and sweetening agents as well as the commonly employed pharmaceutically acceptable additives.

In their quality of phytopharmaceuticals the compounds according to the invention can be employed in various administration forms, as an example aqueous solutions containing or not containing additional additives such as, for instance, talc or clay; powders, including the atomized preparations; sprays, both liquid and solids; suppositories, including the slow-release formulations; granules, including the slow-release formulations; the forms absorbed on inert materials or ion-exchange resins; capsules and microincapsulated preparations. All of these administration forms are well familiar to the art skilled technician.

Accordingly, the compounds of the present invention may also usefully be employed for the preservation of food-stuffs such as, for instance, citrus-fruits or potatoes; as, contrary to a lot of commonly employed substances, e.g. the bis-phenyl, they are effective antibiotic agents displaying a very low toxicity. The compounds of the invention can be prepared by different procedures. Thus, for instance, the amino group of a compound of formula II

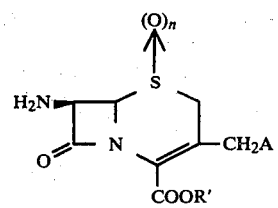

wherein R', A and n are as above defined, is acylated with a suitable N-acylating reactant deriving from an acid of formula III

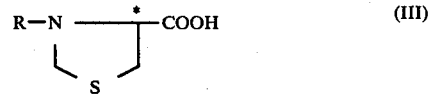

wherein R is as above defined. The protecting groups, if any, must easily be removable under mild conditions. Typical example of a protecting group is the benzyloxycarbonyl radical. Such acylation reactions are well known in the field of penicillins and cephalosporins (see, for instance, Flynn, Cephalosporins and penicyllins, Academic Press, 1972). Also the starting substances of formula II and III are known to the art skilled technician. The choice of the acylating agents will obviously depend on the chemical nature of the substituents R and R', according to the common techniques and principles.

The N-acylating reactants deriving from the compound of formula III above are, for instance, the halides or those obtained through the reaction of III with the carbodiimide or the azide; preferably, an anhydride is employed and, advantageously, a mixed anhydride prepared in situ by reaction with ethyl- or isobutylchlorocarbonate, or pivaloyl chloride.

The choice of the reaction solvent and conditions, which essentially depend on the selected N-acylating agent, is a familiar task for the art expert. As an example, if the acylating agent is a mixed anhydride, the reaction may be carried out in an organic solvent selected from ethyl acetate, dimethylformamide, diethyl ether, tetrahydrofuran, dioxane, methylene chloride or analogous inert solvents; the temperature may be comprised between about −40° C. and about the room temperature and, preferably, it is comprised between about −20° and −30° C.

A further advantageous methods for preparing the compounds of formula I comprises reacting the compounds of formula II and III above with silicon tetrachloride, according to Italian patent application No. 29445 A/77. The compounds of the invention can be isolated by means of techniques well known in the field of penicillins and cephalosporins such as, for instance, by crystallization, liophylization or spray-drying. A suitable isolating procedure comprises the absorption on chemically inert or activated material, as an example the ion exchanging resins; this procedure may be particularly useful when the obtained derivative must be used as food for animals or as phytopharmaceuticals.

The following examples are provided with the purpose of better illustrating the invention but in no way they must be construed as a limitation of the invention itself.

The 7-amino-cephalorsporanic acid will hereinbelow be indicated with the abbreviation 7-ACA; the 7-aminodesacetoxycephalosporanic acid with the abbreviation 7-ADCA.

EXAMPLE 1

7-(1,3-Thiazolidine-4-yl)-carboxamido-desacetoxycephalosporanic acid sodium salt (compound of formula I wherein R=H; R'=Na; A=H; n=0)

25.0 Grams of 7-ADCA suspended in 185 ml of methylene chloride chilled to −40° C. were added under vigorous stirring 13.0 g of n-propylamine, taking care that the temperature were maintained at around −25° C. After 30 minutes at this temperature, 26.0 g of trimethylchlorosilane were slowly poured into the reaction flask and, at the end of the addition, the temperature was between −5° C. and 0° C. After stirring for 30 minutes and cooling to −10° C., 18.5 g of N,N-dimethylaniline and 87.5 g of the hydrochloride of the 7,3-thiazolidine-4-yl-carboxylic acid chloride were rapidly added, whereby the temperature was allowed to raise to the ambient values. The resulting mixture was stirred for two hours at room temperature, added with 500 ml of water, stirred for 30 minutes in order to completely remove the trimethylsilyl group and cautiously brought to pH 7–7.5 with aqueous 10% sodium hydroxide.

The lower organic phase was cast off, the upper organic phase was extracted with 100 ml of methyl-isobutyl ketone and 100 ml of diethylether, treated with decolorizing coal (previously washed with hydrochloric acid and water) and filtered under vacuum on Dicalite 438 ®. The so obtained solution was lyophilized thus obtaining a white powder. The I.R. and N.M.R. analysis are in agreement with the desired structure. The T.L.C. (Thin Layer Chromatography) analysis revealed the substantial purity of the compound.

EXAMPLE 2

7-(1,3-Thiazolidine-4-yl)-carboxamido-cephalosporanic acid sodium salt (compound of formula I wherein R=H; R'=Na; A=—O—COCH$_3$; n=0)

29.5 Grams of 1,3-thiazolidine-4-yl-carboxylic acid were suspended in 200 ml of acetone and, under stirring, 24.2 g of triethylamine were added. The mixture was then cooled to −20° C. and added at this temperature with a solution of 24.0 g of pivaloyl chloride in 40 ml of acetone. After keeping at this temperature for 30 minutes, a previously prepared solution of 54.4 g 7-ACA and 24.2 g of triethylamine in 400 ml of chloroform, cooled at −10° C., was poured into the reaction flask and the whole was allowed to react for 30 minutes at −10° C., 1 hour at 0° C. and 3 hours without any external cooling. The solvent was evaporated off under vacuum at a temperature not exceeding 40° C., and the obtained residue was taken up with 200 ml of water containing 10% of sodium hydrogen carbonate. The so obtained mixture was vigorously stirred and brought to pH 1–1.5 with aqueous 15% hydrochloric acid, first extracted with 100 ml of diethyl ether, which was discarded, and then with 300 ml of ethyl acetate. The ethyl acetate extract was twice washed with 100 ml (2×100 ml) of water, dried over sodium sulfate, then the solvent was evaporated off in vacuo at a temperature not exceeding 40° C. A residue was obtained, which was treated with 200 ml of water, cautiously brought to neutrality with aqueous 10% sodium hydroxide, insoluble materials were filtered off from this aqueous solution and the limpid filtrate was lyophilized, thus giving the desired end compound.

The I.R. and N.M.R. analysis are in agreement with the desired structure. The TLC-analysis [Silicagel F 254 plate (Merck); eluting system: n-butanol/acetic acid/water=30/10/10 (v/v); visualization: UV-light (λ=254 nm) and iodine vapors] revealed the substantial purity of the compound.

EXAMPLE 3

7-(1,3-Thiazolidine-4-yl)-carboxamido-cephalosporanic acid hexamethylenetetraamine salt (compound of formula I wherein R=H; R'=the hexamethylenetetraamine cation; A=—O—COCH$_3$; n=0)

1000 Grams of the compound obtained as described in example 1 before treatment with water and sodium hydroxide were suspended in 5 liters of water and the resulting suspension was added under stirring with an about equimolecular amount of hexamethylenetetraamine, thus reaching a pH value of 7–7.5. The resulting solution was filtered from any insoluble, and the obtained filtrate was spray-dried thus obtaining a white, water-soluble powder suitable for veterinary use, either as such or in admixture with integrated feed or drink-water, for the prophylaxis or the treatment of infections caused by pathogeni agents sensitive to the antibiotic.

The obtained powder may usefully be employed also in the formulations for phytopharmaceuticals, alone or with the commonly employed additives. The following composition, to be prepared before use, proved to be particularly effective: compound of example 3: 1 part; soap: 1 part; petroleum: 1 part; water: 100 parts. To be applied by nebulization.

EXAMPLE 4

(7-(1,3-Thiazolidine-4-yl)-carboxamido)-(3-(5-methyl-1,3,4-thiadiazole-2-yl-thio)methyl)-3-cephem-4-carboxylic acid (compound of formula I wherein R=H; R'=H;

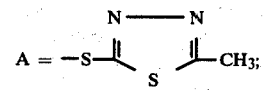

n=0)

A suspension of 0.1 mole of the compound of example 2 in 1000 ml of 0.1 M phosphate buffer (pH 6.4) was added in small portions under stirring with 0.11 mole of 2-methyl-5-mercapto-1,3,4-thiadiazole and 0.15 mole of NaHCO$_3$, taking care that bubbling were not too vigorous. The obtained mixture was heated to 50°–60° C., kept at this temperature for 6 hours, in any case until disappearance of the acetylated compound, then it was cooled and twice washed with 200 ml (2×200 ml) of methyl-isobutyl ketone. After cautiously bringing the pH value to 2.5–3.5, a precipitate was obtained which, after some hours, was filtered, washed with water and dried at a temperature not higher than 40° C. The I.R. N.M.R. analysis are in agreement with the desired structure. The TLC analysis [Silicagel F 254 plate; eluting system: n-butanol/acetic acid/water=30/10/10 (v/v); visualization: UV-light (λ=254 nm) and iodine azide] revealed the substantial purity of the compound.

EXAMPLE 5

(7-(1,3-Thiazolidine-4-yl)-carboxamido)-(3-(5-methyl-1,3,4-thiadiazole-4-yl-thio)methyl)-3-cephem-4-carboxylic acid N-methylglucamine salt (compound of formula I, wherein R=H; R'=the N-methylglucamine cation;

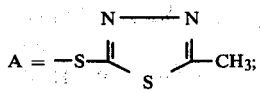

n=0)

1 Mole of the compound of example 4 was suspended in 1000 ml of water and added, under vigorous stirring and continuous control of the pH values, with 1 mole of N-methylglucamine in portions, in any case until a pH value of 7-7.5. The obtained solution was filtered on a sterilizing and de-pyrogenating filter, the filtrate was lyophilized according to the known techniques thus obtaining the title product as a sterile and pyrogen-free powder suitable for intramuscular injections in the veterinary praxis.

EXAMPLE 6

3-(Pyridiniomethyl)-7-(1,3-thiazolidine-4-yl)-carboxamido-3-cephem-4-carboxylate (compound of formula I wherein R=H; R'=negative charge;

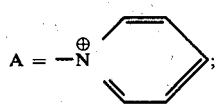

n=0)

A solution of 180 g of the compound of example 2 in 500 ml of water was added under vigorous stirring with 100 ml of pyridine and, subsequently, with 100 g of potassium thiocyanate in small portions. The resulting mixture was brought to pH 6.5 with 85% phoshoric acid and heated under stirring for 6 hours at 60° C. After cooling to room temperature, the reaction mixture was treated with Amberlite LA-1 ® (as the corresponding acetate) and suspended in 25% methyl isobutyl ketone. Three treatments with one liter each time were carried out. The so treated aqueous solution was again extracted three times with 200 ml of methyl-isobutyl ketone (3×200 ml) and was finally lyophilized, thus obtaining a substantially white powder. The I.R. and N.M.R. analysis are in agreement with the desired structure. The TLC analysis [Silicagel F-254 plate; eluting system: ethylacetate/acetic acid=60/20 (v/v), saturated with water; visualization: U.V.-light (λ=254 nm) and iodine vapors] revealed the substantial purity of the compound.

EXAMPLE 7

7-[(N-Pivaloyl)-1,3-thiazolidine-4-yl]-carboxamido-cephalosporanic acid (compound of formula I wherein R=$(CH_3)_3$C—CO; R'=H; A=—O—$COCH_3$; n=0)

10.0 Grams of N-pivaloyl-thiazolidincarboxylic acid were suspended in 50 ml of acetone, then 4.65 g of triethylamine were added. After cooling to −15° C., the suspension was added with 5.5 g of pivaloylchloride in 25 ml of acetone, taking care that the temperature did not raise above −10° C. When the addition was terminated, two drops of 4-methyl-morpholine were added, the mixture was left standing at −15° C. for 20 minutes, then a previously prepared solution of 12.5 g of 7-ACA in 10 ml of water, 20 ml of acetone and 5.0 g of TEA, cooled at −10° C., was rapidly poured into the reaction flask. The resulting mixture was reacted for 4 hours, removing the cooling bath after two hours, thus allowing the temperature to raise to 20° C., then 2.0 g of Dicalite ® were added and the whole was filtered under vacuum. A residue was obtained, which was washed with 20 ml of acetone and 5 ml of water, the obtained solution was filtered from any insoluble and evaporated to dryness in vacuo at a temperature not exceeding 40° C. The obtained reddish oil was dispersed in 100 ml of water, the aqueous dispersion was twice extracted with 50 ml (2×50 ml) of diethyl ether, the ether extracts were discarded and the aqueous phase brought to pH 1 by means of aqueous 10% hydrochloric acid. The resulting emulsion was twice extracted with 100 and 50 ml respectively of ethylacetate, the organic phases were collected, washed with 50 ml of a saturated solution of sodium chloride, dried over sodium sulfate and finally brought to dryness in vacuo, at a temperature not exceeding 40° C. A crystalline solid was obtained, which was filtered, washed with 10 ml of diethyl ether and dried in the air. Yield: 10 g of the title compound. M.p.: 148°-50° C. The TLC analysis gave a unitary spot with Rf value=0.53 [Silicagel plate F 254; eluting system: ethyl acetate/acetone/glacial acetic acid/water=5/2/1/1 (v/v); visualization: iodine vapors]. The structure of the compound was confirmed through N.M.R. analysis in $CDCl_3$ by using TMS (Trimethylchlorosilane) as the internal standard.

δ = 1,3 (s, 9H, tert.-butyl)
δ = 2,2 (s, 3H, $CH_3$—CO)
δ = 3,2–3,7 (m, 4H, S—$CH_2$)
δ = 3,55 (s, 1H, CH—CO)

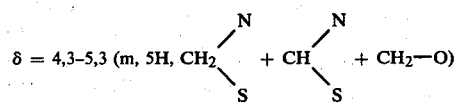

δ = 5,8 (m, 1H, CH—NH)
δ = 7,8 (d, 1H, NH)

s = singlet;
d = doublet;
m = multiplet.

EXAMPLE 8

3-((5-Methyl-1,3,4-thiadiazole-2-yl-thio)methyl)-7-(N-pivaloyl-1,3-thiazolidine-4-yl)-carboxamido-3-cephem-4-carboxylic acid (compound of formula I wherein R=$(CH_3)_3$C—CO; R'=H;

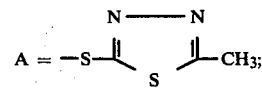

n=0)

10.0 Grams of N-pivaloyl-1,3-thiazolidine-4-yl-carboxylic acid were suspended in 50 ml of acetone together with 4.65 g of triethylamine, the resulting suspension was cooled to −15° C. and subsequently added dropwise with a solution of 5.5 g of pivaloyl chloride in 25 ml of acetone. 2 drops of 4-methyl-morpholine were also added. After standing for 20 minutes at −15° C., a previously prepared solution of 15.5 g of 7-amino-3-[(5-methyl-1,3,4-thiadiazole-2-yl-thio)-methyl]-Δ³-cephem-4-carboxylic acid in 10 ml of water and 20 ml of acetone was rapidly poured into the reaction flask, whereby the temperature was raised to 0° C. and the pH brought to 8.5 by means of triethylamine. The resulting mixture was left standing two hours at 2° C. and two further hours allowing the temperature to raise to 20° C. The formed insoluble was removed by filtration, washed on filter with 10 ml of acetone, the collected acetone solutions were diluted with 100 ml of water and twice extracted with 100 ml (2×100 ml) of a 1/1 (v/v) mixture of ethyl acetate/diethyl ether. The aqueous phase was brought to pH 3 by means of aqueous 10% hydrochloric acid, extracted three times with 50 ml (3×50 ml) of ethyl acetate, the ethyl acetate phase was washed with 50 ml of an aqueous saturated solution of NaCl, dried over sodium sulfate and evaporated in vacuo at a temperature not exceeding 40° C. The obtained residue was taken up with 50 ml of diethyl ether, thus obtaining a crystalline solid which was filtered, washed with 20 ml of diethyl ether and dried in the air. Yield: 6.5 g of the title compound. M.p.: 158°–60° C.

The TLC analysis gave a unitary spot with Rf value=0.49 [Silicagel F 254 plate; eluting system: ethyl acetate/acetone/glacial acetic acid/water=5/2/1/1 (v/v); visualization=iodine vapors].

The structure of the compound was confirmed through N.M.R. analysis in CDCl₃, using TMS (Trimethylchlorosilane) as the internal standard.

| |
|---|
| δ = 1,3 (s, 9H, tert.-butyl) |
| δ = 2,1 (s, 3H, CH₃) |
| δ = 2,75 (s, 2H, CH₂—S—Eterociclo) |
| δ = 3,0–3,8 (m, 5H, CH₂—S + CH—CONH) |
| 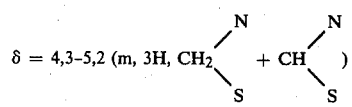 |
| δ = 5,8 (m, 1H, CH—NH) |
| δ = 7,3 (s, 1H, COOH) |
| δ = 7,9 (d, 1H, NH) | s = singlet;
d = doublet;
m = multiplet.

We claim:

1. A compound with antibiotic activity of formula I

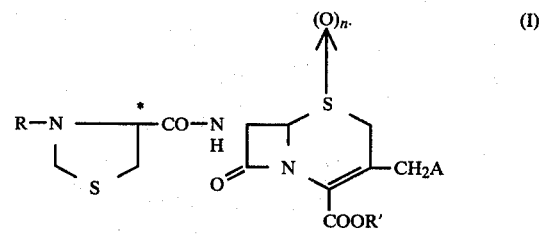

wherein:

R is hydrogen or pivaloyl;

A is selected from the group consisting of hydrogen, acetoxy, 5-methyl-1,3,4-thiadiazol-2-yl thio-, 5-methyl-1,3,4,-thiadiazol-5-yl thio- and the pyridinium cation;

R' is hydrogen, or an inorganic or organic cation which is the cation from sodium, potassium, calcium, magnesium, aluminum, zinc, silver or a cation deriving from an organic base, which is dibenzylamine, N,N-dibenzylethylenediamine, glucamine, N-methylglucamine, hexamethylenetetramine, 2-amino-2-hydroxymethyl-1,3-propanediol, arginine, lysine, proline or carnitine;

or when A is the pyridinium cation, R' is a negative charge;

—n is 0 or 1;

the carbon atom of the thiazolidine ring marked with an asterisk has the D- or L- or racemic configuration;

and salts thereof with a pharmaceutically acceptable acid, which is citric, ascorbic, maleic, acetic, hydrochloric, nitric, hydrobromic or sulfuric acid.

2. A compound as defined in claim 1, wherein R, R' and A represent hydrogen and n is zero.

3. A compound as defined in claim 1, wherein R and A represent hydrogen, R' is sodium and n is zero.

4. A compound as defined in claim 1, wherein R and R' represent hydrogen, A is acetoxy and n is zero.

5. A compound as defined in claim 1, wherein R represents hydrogen, R' is sodium, A is acetoxy and n is zero.

6. A compound as defined in claim 1, wherein R represents hydrogen, R' is the hexamethylenetetraamine cation, A is acetoxy and n is zero.

7. A compound as defined in claim 1, wherein R and R' represent hydrogen, A is 5-methyl-1,3,4-thiadiazole-2-yl-thio- and n is zero.

8. A compound as defined in claim 1, wherein R represents hydrogen, R' is the N-methylglucamine cation, A is 5-methyl-1,3,4-thiadiazole-5-yl-thio and n is zero.

9. A compound as defined in claim 1, wherein R is pivaloyl, R' represents hydrogen, A is acetoxy and n is zero.

10. A compound as defined in claim 1, wherein R is pivaloyl, R' represents hydrogen, A is 5-methyl-1,3,4-thiadiazole-5-yl-thio- and n is zero.

11. A pharmaceutical composition for human, veterinary and agricultural use, which contains as the active ingredient an antibiotically effective amount of at least one compound as defined in claim 1 in admixture with at least one pharmaceutically acceptable carrier.

12. A compound according to claim 1, wherein R is hydrogen, A is the pyridinium cation, n is zero and R' is a negative charge.

* * * * *